(12) United States Patent
Neittaanmäki-Perttu et al.

(10) Patent No.: US 10,478,071 B2
(45) Date of Patent: Nov. 19, 2019

(54) MEDICAL IMAGING

(71) Applicant: REVENIO RESEARCH OY, Vantaa (FI)

(72) Inventors: Noora Neittaanmäki-Perttu, Helsinki (FI); Mari Grönroos, Helsinki (FI); Pekka Neittaanmäki, Jyväskylä (FI); Ilkka Pölönen, Jyväskylä (FI); Hannu-Heikki Puupponen, Muurame (FI)

(73) Assignee: REVENIO RESEARCH OY, Vantaa (FI)

( * ) Notice: Subject to any disclaimer, the term of this patent is extended or adjusted under 35 U.S.C. 154(b) by 827 days.

(21) Appl. No.: 15/102,398

(22) PCT Filed: Dec. 12, 2014

(86) PCT No.: PCT/FI2014/050990
§ 371 (c)(1),
(2) Date: Jun. 7, 2016

(87) PCT Pub. No.: WO2015/086911
PCT Pub. Date: Jun. 18, 2015

(65) Prior Publication Data
US 2016/0310008 A1 Oct. 27, 2016

(30) Foreign Application Priority Data
Dec. 13, 2013 (FI) ...................... 20136265

(51) Int. Cl.
*A61B 5/00* (2006.01)
*G06T 7/00* (2017.01)
(Continued)

(52) U.S. Cl.
CPC .......... *A61B 5/0075* (2013.01); *A61B 5/0077* (2013.01); *A61B 5/444* (2013.01);
(Continued)

(58) Field of Classification Search
CPC .......... A61B 5/0075; A61B 6/00; A61B 1/00; A61B 5/0077; A61B 5/444; A61B 2576/00
See application file for complete search history.

(56) References Cited

U.S. PATENT DOCUMENTS 8,391,961 B2 * 3/2013 Levenson ............ A61B 5/0059
356/300
2012/0314920 A1 12/2012 Prigent et al.

FOREIGN PATENT DOCUMENTS

| JP | H0755447 A | 3/1995 |
| JP | 2013509629 A | 3/2013 |
| WO | WO-00/02156 A1 | 1/2000 |

OTHER PUBLICATIONS

Pölönen, I., "Discovering Knowledge in Various Applications with a Novel Hyperspectral Imager", University of Jyväskylä Studies in Computing, vol. 184, Dec. 2013, ISBN 978-951-39-5538-0 (published online Dec. 9, 2013) (49 pages).

(Continued)

*Primary Examiner* — Joel Lamprecht
(74) *Attorney, Agent, or Firm* — Robert P. Michal, Esq.; Carter, DeLuca & Farrell LLP

(57) ABSTRACT

A medical imaging method includes imaging a target with a hyperspectral imaging system in order to obtain imaging data. There is provided a method in medical imaging. In the method, a target is imaged with a hyperspectral imaging system in order to obtain imaging data. The obtained imaging data is pre-processed by spatial and spectral averaging. A number of endmembers to be determined from the pre-processed imaging data is selected. The endmembers are extracted from the pre-processed imaging data based on vertex component analysis on the pre-processed imaging (Continued)

data and the selected number of endmembers, said endmembers defining an extremity of projections of the pre-processed imaging data in a subspace spanned by the endmembers. At least one abundance map is generated of the selected number of endmembers in the pre-processed imaging data using a filter vector algorithm on the extracted endmembers and the imaging data.

19 Claims, 2 Drawing Sheets

(51) Int. Cl.
*G06T 3/40* (2006.01)
*G06T 5/00* (2006.01)

(52) U.S. Cl.
CPC ............... *G06T 3/40* (2013.01); *G06T 5/002* (2013.01); *G06T 7/0012* (2013.01); *A61B 2576/00* (2013.01); *G06T 2207/30088* (2013.01); *G06T 2207/30096* (2013.01); *G06T 2210/22* (2013.01)

(56) References Cited

OTHER PUBLICATIONS

Neittaanmäki-Perttu, N., et al., "Detecting Field Cancerization using a Hyperspectral Imaging System", Lasers in Surgery and Medicine, Sep. 2013, vol. 45, No. 7, pp. 410-417 page, (Total of 8 pages).
Dobigeon, N., et al., "Joint Bayesian Endmember Extraction and Linear Unmixing for Hyperspectral Imagery", IEEE Transactions on Signal Processing, Nov. 2009, vol. 57, No. 11, pp. 4355-4368, (Total of 15 pages).
Nascimento, J. M. P., et al., "Vertex Component Analysis: A Fast Algorithm to Unmix Hyperspectral data", IEEE Transactions on Geoscience and Remote Sensing, Apr. 2005, vol. 43, No. 4, pp. 898-910, (Total of 14 pages).
Bowles, J., et al., "Use of Filter Vectors in Hyperspectral Data Analysis", Proceedings of SPIE vol. 2553, Infrared Spaceborne Remote Sensing III, Sep. 29, 1995, pp. 148-157, (Total of 10 pages).
International Search Report for PCT/FI2014/050990 dated Apr. 2, 2015 (6 pages).
Notification of Reasons for Refusal issued by the Japanese Patent Office in relation to Japanese Application No. 2016-558280 dated Aug. 9, 2018 (4 pages) along with English language translation (3 pages).

\* cited by examiner

MEDICAL IMAGING

CROSS-REFERENCE TO RELATED APPLICATIONS

This application is a National Phase Entry under 35 USC § 371 of PCT Patent Application Serial No. PCT/FI2014/050990 filed Dec. 12, 2014, which claims the benefit under 35 USC § 119 to Finnish Patent Application No. 20136265, filed Dec. 13, 2013, the disclosure of each of these applications are expressly incorporated herein by reference in their entireties.

FIELD OF THE INVENTION

The invention relates to medical imaging and more particularly to imaging in dermatology.

BACKGROUND OF THE INVENTION

Skin cancers are the most common cancer type in western world. Currently, between two to three million non-melanoma and 132,000 melanoma cases are reported globally each year (WHO). Melanoma is the most common cancer for young adults 25-29 years old. About 90 percent of non-melanoma skin cancers and 86 Lentigo Maligna (LM) is an early form of melanoma in which the malignant cells are confined to the tissue of origin, the epidermis, hence it is often reported as in situ melanoma. It occurs in sun damaged skin. Lentigo Maligna Melanoma (LMM) is diagnosed when the malignant melanoma cells have invaded into the dermis and deeper layers of skin. The prognosis for invasive LMM is poorer than in LM. Clinically LM cannot be differentiated from invasive LMM.

For both, LM and LMM, surgical removal is the first treatment. It is essential to remove all damaged skin cells, since even a few damaged cells left behind can launch cancer again. The borders of LM and LMM are often hard to define by eye due to subclinical extension of the lesion borders seen only in histopatholgical sampling. Often a re-excision is required.

No accurate in vivo methods currently exist to accurately identify the areas of tumor cell spread. Early accurate diagnosis will increase patients' survival and decrease cost of treatment dramatically.

State-of-the-art method utilized clinically is based examination lesions with dermato-scope. These devices are practically optical magnifiers which have from one to three different integrated illumination choices. These devices can be used together with normal digital cameras. This type of equipment acquires a high-resolution image with three wide spectral bands (red, green and blue).

Hyperspectral imaging offers accurate spatial and spectral information about imaged skin lesions. FIG. 1 illustrates a hyperspectral datacube. As seen in FIG. 1, a hyperspectral image contains from couple of dozen to thousands monochromatic images which are taken within a short period of time and from same location. A set 104 of images is typically called a hyperspectral data cube. These monochromatic images are taken at 70 different wavelengths. Thus, basically, every pixel in a hyperspectral image represents the intensity of light in a certain spot at a certain wavelength. A set of pixels trough hyperspectral data cube forms a spectrum 106.

BRIEF DESCRIPTION THE INVENTION

An object of the present invention is to provide a method, an arrangement and a computer program product in medical imaging so as to alleviate at least of the above disadvantages. The objects of the invention are achieved by a method, an arrangement and a computer program product that are characterized by what is stated in the independent claims. The preferred embodiments of the invention are disclosed in the dependent claims.

According to an aspect there is provided a method in medical imaging, comprising: imaging a target with a hyperspectral imaging system in order to obtain imaging data; pre-processing the obtained imaging data by spatial and spectral averaging; selecting a number of endmembers to be determined from the pre-processed imaging data; extracting the endmembers from the pre-processed imaging data based on vertex component analysis on the pre-processed imaging data and the selected number of endmembers, said endmembers defining an extremity of projections of the pre-processed imaging data in a subspace spanned by the endmembers; generating at least one abundance map of the selected number of endmembers in the pre-processed imaging data using a filter vector algorithm on the extracted endmembers and the imaging data.

According to an aspect there is provided an arrangement comprising means to perform a method according to an aspect.

According to an aspect there is provided an arrangement for medical imaging comprising: at least one processor and at least one memory including a computer program code, wherein the at least one memory and the computer program code are configured to, with the at least one processor, cause the arrangement at least to: obtain imaging data of a target imaged by a hyperspectral imaging system; pre-process the obtained imaging data by spatial and spectral averaging; select a number of endmembers to be determined from the pre-processed imaging data; extract the endmembers from the pre-processed imaging data based on vertex component analysis on the pre-processed imaging data and the selected number of endmembers, said endmembers defining an extremity of projections of the pre-processed imaging data in a subspace spanned by the endmembers; generate at least one abundance map of the selected number of endmembers in the pre-processed imaging data using a filter vector algorithm on the extracted endmembers and the imaging data.

According to an aspect there is provided a computer program product embodied on a distribution medium readable by a computer and comprising program instructions which, when loaded into an apparatus, execute the method according to an aspect.

According to an aspect there is provided an apparatus, comprising processing means configured to cause the apparatus to perform the method according to an aspect.

Some of the embodiments provide improvements in medical imaging of subjects such that a presence of tissue in the subject may be determined even if the tissue is not visible to the eye. For example, borders of malignant and healthy tissue may be determined accurately without surgical procedures even if some part of the malignant tissue is not visible in the subject to the human eye.

Some embodiments provide clarifying border areas of dermatological lesions including LM and LMM, and separating lesions from one another.

BRIEF DESCRIPTION OF THE DRAWINGS

In the following the invention will be described in greater detail by means of preferred embodiments with reference to the accompanying drawings, in which.

DETAILED DESCRIPTION OF THE INVENTION

Figure 1:
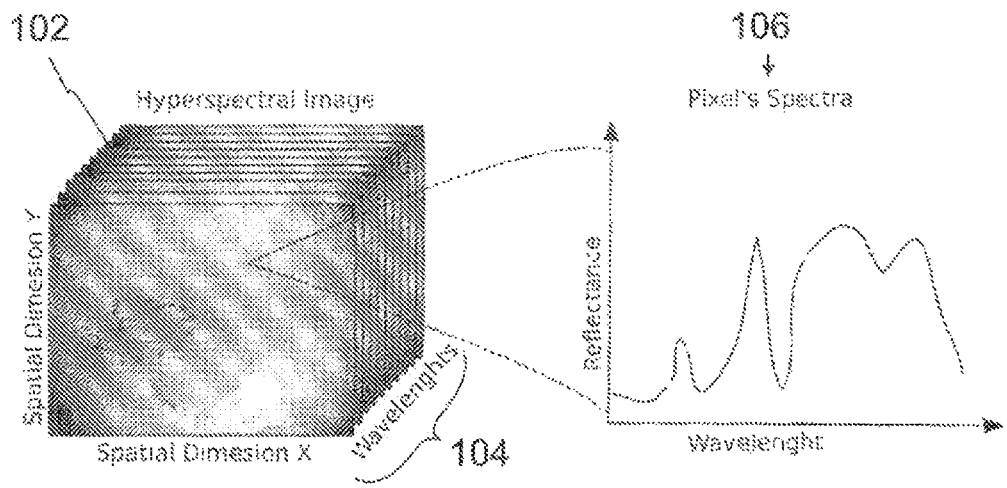
FIG. 1 is illustrates a hyperspectral datacube.

The following embodiments are exemplary. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Various embodiments concern medical imaging of subject or a part of the subject. The subject may be human or an animal. The medical imaging forms imaging data of the subject. The imaging data is processed as described in the embodiments such that information may be extracted from the imaging data to determine presence of a specific type of tissue(s) in the subject and/or determine borders of different types of tissues. Thanks to the hyperspectral imaging, presence of tissues may be determined even if they are not visible to the human eye. This allows clinicians to obtain information from the medical condition of the subject without surgical procedures. The information allows the clinician to plan surgical procedures better beforehand such that the procedure itself is more likely to succeed. In one example borders of malignant tissue may be determined accurately beforehand which allows the clinician to plane the surgical operation for removal of the malignant tissue such that the removal is complete. This is particularly important for malignant tissues that are a risk to the health of the subject.

In the hyperspectral imaging reflections of light from the subject are obtained in a hyperspectral camera. The hyperspectral camera forms imaging data. The formed imaging data may be a hyperspectral datacube formed by hyperspectral images of the subject. Each pixel of the hyperspectral datacube has a plurality of light intensity values each corresponding to a portion of the spectrum, e.g. a specific wavelength(s). The light intensity values per pixel depend on the resolution applied to measurement over the spectrum in the hyperspectral camera. Different wavelengths of light may reflect from the target at different depths, whereby the hyperspectral images may be used to determine tissue types in the subject at different depths.

The hyperspectral imaging may use a wavelength range and wavelength resolution that may be determined according to the purpose of the medical imaging and type of tissue(s) in the subject. A higher resolution for the wavelengths may be used if a higher accuracy is needed. On the other hand, lower resolution for the wavelengths may be used if sufficient accuracy may be provided by the lower number of wavelengths. A single pixel in a hyperspectral datacube therefore includes intensity of light for a plurality of wavelengths defined by the resolution in the wavelength range. The pixel represents light intensity measured from a single location in the subject. An image plane of the subject includes pixels of the hyperspectral data cube. Each pixel corresponds to a location on the subject. The location may be defined in two-dimensional coordinates, e.g. in X-Y coordinates.

Figure 2A:
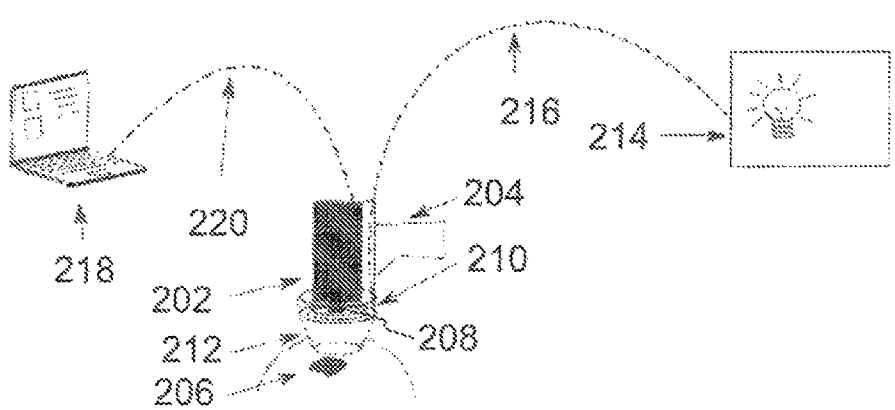
FIG. 2a illustrates an arrangement for medical imaging according to an embodiment.
Figure 2B:
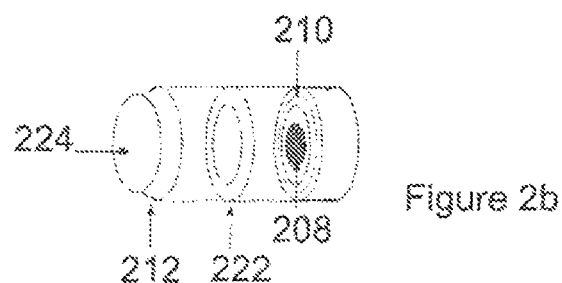
FIG. 2b illustrates a structure of hyperspectral camera according to an embodiment.

An arrangement according to an embodiment is illustrated in FIG. 2a. The arrangement will now be described with reference to both FIGS. 2a and 2b that illustrates a structure of a hyperspectral camera according to an embodiment. The structure illustrated in FIG. 2b may be used in a hyperspectral camera of the arrangement of FIG. 2a. The structure includes a cone 212 and a light source 210, a camera opening 208, e.g. a camera lens, that allows light reflected from a target to enter the camera for forming imaging data, and a diffuse sheet 222 arranged within the cone. The light source may be arranged to the end of the cone that is remote from the target, when the cone is installed to the hyperspectral camera for imaging the target. The light source may be arranged around the camera opening for illuminating the target uniformly. The cone directs the light from the light source to the target through an opening 224 of the cone in the end of the cone opposite to the camera opening. In this way the light to the target is directed by both the diffuse sheet and the cone. The hyperspectral camera may be based on a piezo-actuated Fabry-Perot interferometer.

The hyperspectral camera 202 may be installed to a handle 204. A user such as a clinician may grab the handle for positioning the hyperspectral camera over the target 206 that is on the subject. The hyperspectral camera may be connected to the handle by screws or the handle and the camera may be enclosed into a single body. The body may be any material suitable for clinical work. These materials may include various plastic compositions, for example.

The cone 212 is arranged around the light source and to extend towards the target. In this way interfering external light sources may be excluded and a consistent subject distance to the camera may be maintained. The cone and the camera maybe threaded such that the cone maybe easily changed and fixed to its position during imaging. The cones may be provided with several diameters for matching differed targets and corresponding locations, examples of which are skin abnormalities in different locations in the human body.

The light source may be a circular light source, i.e. a ringlight, such that the target is uniformly illuminated. In an embodiment the light source is a fiber-optic ring-light that is connected to a remote light source 214 by a light fibre 216. The light-fiber allows light emitted by the remote light source to travel to the fiber-optic ring-light arranged around the camera opening. The remote light source may be a halogen light, for example. The remote light source allows a simple and light construction of the handheld hyperspectral camera. Since the light source is remote, i.e. external, from the handheld camera unit, conveying of heat from the light source to the handheld hyperspectral camera and the target being imaged may be prevented or at least mitigated. The light source may be powered by a power supply arranged also remote from the handheld hyperspectral camera to facilitate the simple and light construction and prevent conveying of the heat. The diffuse sheet may be positioned between the light source and the target such that the diffuse sheet separates the light source from the target. Preferably the diffuse sheet is positioned inside the cone closely against the cone such that light from the light source travels to the target through the diffuse sheet and stray light is prevented or at least minimized. The diffuse sheet allows a more consistent light distribution pattern on the target. As a diffuse sheet can be used a sheet of paper or an optical diffuser manufactured from glass. The size, e.g. diameter, and shape of the diffuse sheet may be fitted to the size, e.g. diameter, and the shape of the cone to minimize the stray light. Additionally the diffuse sheet may be sealed to its position within the cone to prevent stray light from the light source to the target. The sealing may be provided by suitably shaped seals of elastic material and/or silicone paste.

A computer 218, for example a laptop computer, may be connected to the hyperspectral camera such that the computer may receive imaging data from the hyperspectral camera. The connection 220 between the hyperspectral camera and the computer may be any wired or wireless connection capable of communicating imaging data from the hyperspectral camera to the computer. Examples of wireless connections comprise Bluetooth and IEEE 802.11 based Wireless Local Area Network connections. Examples of wired connections comprise Universal Serial Bus and Ethernet. A benefit of a wired connection is that the hyperspectral camera may be powered through the wired connection. On the other hand the wired connection may provide a faster connection setup and a higher reliability than wireless connections that may be prone to interference and often require human actions on the computer user interface in order to setup the wireless connection.

A handheld hyperspectral camera according to an embodiment includes a handle, a hyperspectral camera and interfaces 220, 216 to a remote data processing device and to a remote light source that are both external to the hyperspectral camera. The remote data processing device may be a computer for example. The interfaces may provide connections to the remote data processing device and the light source as described above. Since the processing of the imaging data may be performed at least partly in the remote data processing unit, e.g. a computer that is remote from the handheld camera, the handheld camera unit may be implemented with a very low processing capacity and power consumption. When also the light source is located in an external unit that is remote from the handheld camera, the handheld camera unit may be designed to have a simple structure, low number of components and a light weight. In this way the camera may be made particularly suitable for clinical work. Moreover, when one or both of the light source and data processing are located in external units from the handheld camera which have their own power supplies, the power consumption of the handheld camera unit may be kept small such that the handheld camera unit may be powered by a low Direct Current voltage from a transformer connected to the electric mains or even by small batteries.

Figure 3:
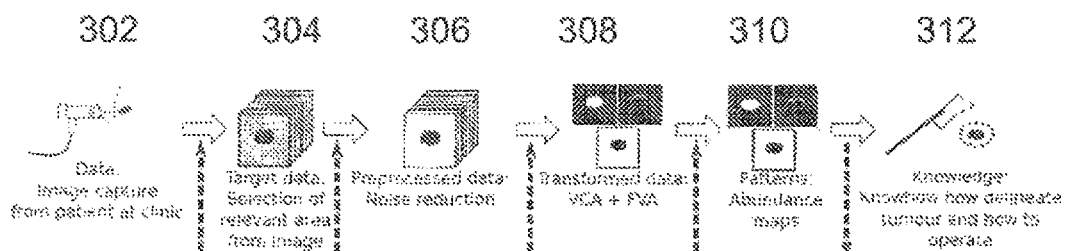
FIG. 3 illustrates a process according to an embodiment.

FIG. 3 illustrates a process according to an embodiment. The process may be performed by one or more entities illustrated in the arrangement of FIG. 2a. In 302 imaging data may be obtained from a hyperspectral camera. Preferably the camera operates as a full frame imager. In this way the object may be imaged faster than if a camera based on bush-broom imaging was used. The bush-broom imaging refers to forming an image data from the object line by line. The imaging data may comprise a hyperspectral data cube. The hyperspectral camera may be a piezo-actuated Fabry-Perot interferometer. The hyperspectral data cube may be formed using the piezo-actuated Fabry-Perot interferometer by successively varying an interferometer setting of the interferometer. The interferometer setting may comprise a gap between mirrors. In a hyperspectral datacube, a pixel of the datacube comprises an intensity of light at a specific location on an imaged target for a specific wavelength of the spectrum.

The following table shows specifications of the hyperspectral camera based on Fabry-Perot interferometer for a practical implementation of the hyperspectral imaging arrangement.

| Parameter | |
|---|---|
| Horizontal and vertical FOV (deg.) | >36,>26 |
| Nominal focal length (mm) | 9.3 ± 3 |
| Wavelength range (nm) | 500-885 |
| Spectral resolution at FWHM (nm) | 9-40 |
| Adjustable spectral resolution step | <1 |
| f-number | <6.7 |
| Maximum spectral image size (pixels) | 2592 × 1044 |
| Spectral image size with default binning (pixels) | 320 × 240 |
| Camera dimensions (mm) | 62 × 66 × 219 |
| Weight (g) (camera only) | <450 |
| Weight with holder (g) | approx. 1000 |

The hyperspectral camera based on Fabry-Perot interferometer provides the wavelength range from approximately 500 to 900 nanometers, with a maximum spatial resolution of 2592 pixels by 1944 pixels. The hyperspectral camera may perform pixel binning, for example four times four pixel binning to produce imaging data having a final image plane resolution of 320 by 240 pixels. Pixel binning refers to pre-processing of the pixels such that effects of minor observation errors may be reduced. Accordingly, it is possible to apply some pre-processing to the imaging data already in the hyperspectral camera. On the other hand, all the processing, including pre-processing may be performed in an external unit, for example a computer. In the pixel binning original data values that fall in a given interval, a bin, are replaced by a value representative of that interval, often the central value. In this way the pixels may be averaged. Depending on the spectral resolution, the imaging data may comprise from 40 to 60 usable bands of spectral data.

In 304 and 306 the imaging data is pre-processed by spatial and spectral averaging. In spatial averaging each spectra may be calculated as a mean value of its nine nearest neighbours and in spectral averaging each waveband may be calculated as mean value of its two nearest neighbours. This may also be referred to as averaging blurring. The imaging data may be cropped to omit any imaging data, for example imaging data that includes pixels from the cone. In this way only the immediate region of interest may be included in the imaging data for efficiency of the processing. In averaging blurring, the imaging data may be processed by a spatial domain linear filter in which each pixel in the resulting image has a value equal to the average value of its neighboring pixels in the input image. The averaging blurring may be applied to the imaging data to even effect of the noise. The blurring may be performed in three times three pixel blocks over image plane.

The pre-processed imaging data may be then spectrally unmixed and inverted in 308 and 310.

An assumption behind spectral unmixing is that the spectrum at a given pixel of the imaging data is a mixture of reflections of light from different types of tissue present in the target being imaged. A linear mixing model may be used to describe the mixing of the reflections. The linear mixing model applied to the imaging data obtained by the hyperspectral imaging assumes the detected spectrum for each pixel to consist of a linear combination of substance-originated constituent spectra, termed endmembers. The substance may be a specific type of tissue, for example healthy tissue, malignant tissue, skin, LM or LMM. The linear mixing model may be used to devise a reverse operation, unmixing, such that the different tissues in the imaging data may be effectively identified.

The linear mixing model may be expressed as $$x[\lambda_n] = \sum_{i=1}^{M} a_i s_i[\lambda_n] + w[\lambda_n]$$

where x is the detected spectrum, a is an abundance coefficient for endmember s, M is the number of endmembers and w is noise term. Expanding LMM to all observed pixel spectra, we arrive at matrix form $$X = AS + W,$$

where $$X = (x[\lambda_1], x[\lambda_2], \ldots x[\lambda_N])^T, A = (a_1, a_2, \ldots, a_M),$$

$$S = \begin{pmatrix} s_1[\lambda_1] & s_2[\lambda_1] & \ldots & s_M[\lambda_1] \\ s_1[\lambda_2] & s_2[\lambda_2] & \ldots & s_M[\lambda_2] \\ \vdots & \vdots & \ldots & \vdots \\ s_1[\lambda_N] & s_2[\lambda_N] & \ldots & s_M[\lambda_N] \end{pmatrix},$$

and $W = (w[1], w[2], \ldots w[N])^T$, where N is the number of wavelengths and A is an abundance map.

Goals of unmixing processes are to estimate these constituent spectra, and their relative abundance for each pixel. Given these abundance coefficients, new images displaying the relative occurrence of a given endmember within the scene can be drawn, usually termed abundance maps.

In 308, the pre-processed imaging data may be unmixed by applying Vertex Component Analysis (VCA) to the pre-processed data. The VCA is outlined in J. Nascimento et al.: J. Nascimento and J. Dias, "Vertex Component Analysis: A fast algorithm to unmix hyperspectral data", IEEE Transactions on Geoscience and Remote Sensing, vol. 43, no. 4, pp. 898-910, 2005.

A number of endmembers to be determined from the pre-processed imaging data may be selected for the VCA. The number of endmembers may be at least two, but also more, for example 3, 4, 5, 6 or any number of endmembers. The endmembers may be extracted from the pre-processed imaging data based on the VCA and the selected number of endmembers. The endmembers may define an extremity of projections of the pre-processed imaging data in a subspace spanned by the endmembers.

The VCA assumes presence of pure pixels S in the input data X, and proceeds by performing iterative orthogonal projections of the data onto subspace spanned by previously determined endmembers. A pure pixel may be referred to a pixel obtained by imaging a tissue having a uniform structure. The structure may be a uniform structure, when the imaged tissue is substantially of a single material. Accordingly, the spectrum in a pure pixel represents only a certain material or substance, for example a healthy tissue or a malignant tissue. The extremity of this projection is taken as being the new endmember signature. This process repeats until M endmembers have been extracted.

As such, the assumption of pure pixels existing is a strong one, and not necessarily true in many types of data. For purpose of discovering material differences present within the scene imaged in contrast to finding endmember spectra directly usable for substance identification, the behavior of selecting the most pure pixel spectra as the endmember signatures may be sufficient.

In 310, at least one abundance map, A, may be generated. The pre-processed imaging data may be converted into one or more abundance maps. It is possible to derive an abundance map corresponding to each endmember. The abundance maps may be generated using a non-negative least squares inversion or a Filter Vector Algorithm (FVA). The FVA is described in J. Bowles, P. Palmadesso, J. Antoniades, M. Baumback and L. Rickard, "Use of filter vectors in hyperspectral data analysis," Proc. SPIE, pp. 148âAT157, 1995.

The FVA is computationally less expensive and therefore preferred. The FVA is applied on the extracted endmembers and the imaging data. The abundance maps indicate an occurrence of the endmembers in the imaging data. The occurrence of the endmembers may be used to determine histological properties of the target. In this way information may be provided for use in diagnosis and treatment.

In the FVA, set of filter vectors F are formed, which are used to estimate abundance coefficients. The Estimation may be performed as follows:

$$A = FX,$$

where $$F = (RS)^{-1}R \text{ and } R = S^T - (J/N * S)^T,$$

where J is N×N unit matrix, A is an abundance map, and N is the number of wavelengths.

In 312, the one or more abundance maps obtained in 310 may be used to determine a presence of tissue in the subject may be determined even if the tissue is not visible to the eye. The abundance map illustrates borders of the tissue in the target. In this way the areas in the target, where the tissues is present may be determined. The tissue may be healthy or malignant. The malignant tissue may comprise a dermatological lesion. Examples of the dermatological lesions comprise LM and LMM. The abundance maps may be displayed on a display device, for example a computer display. When more than one, for example, 2, 3, 4, 5, 6 or any number, of abundance maps are obtained each corresponding to a different tissue in the target, borders in the target for each type of tissue may be determined on the basis of the abundance maps whereby areas in the target corresponding to each type of tissue may be determined.

In an embodiment the abundance maps may be used for diagnosis of at least one of LM and LMM. A clinician may operate an arrangement according to an embodiment that produces one or more abundance maps to be used in the diagnosis. The abundance maps may be viewed on a display to help the clinician in the diagnosis.

It should be appreciated that steps of the method according to an embodiment may be performed in different entities of the arrangement illustrated in FIG. 2a. Accordingly, some of the steps may be performed by the computer and some of the steps may be performed by the hyperspectral camera. Preferably the hyperspectral camera forms 302 imaging data that is sent to the computer to be processed in one or more of the steps 304 through 312.

It should be appreciated that in a clinical setting, the rapid determination of the potentially affected skin area is of utmost importance. Towards this end, the computational complexity of the utilized processing methods has to be given careful consideration. In this respect, VCA has been shown to provide savings of one to two orders of magnitude in comparison against N-FINDR described in J. Nascimento et al.

The combination of the VCA and FVA is particularly suitable for clinical work due to the processing of imaging data requiring only a few second of processing in a conventional laptop computer.

The images in FIGS. 4, 5 and 6 have been taken from in vivo subjects before without any surgical procedures. Abundance maps in the images have been generated using hyperspectral imaging method described in various embodiments herein. The illustrated abundance maps have been confirmed by histopathological sampling. In the images, lesion borders may be identified for accurate removal of the lesions. LM may be differentiated from invasive LMM for accurate non-invasive diagnosis.

Figures 4A, 4B, 4C:
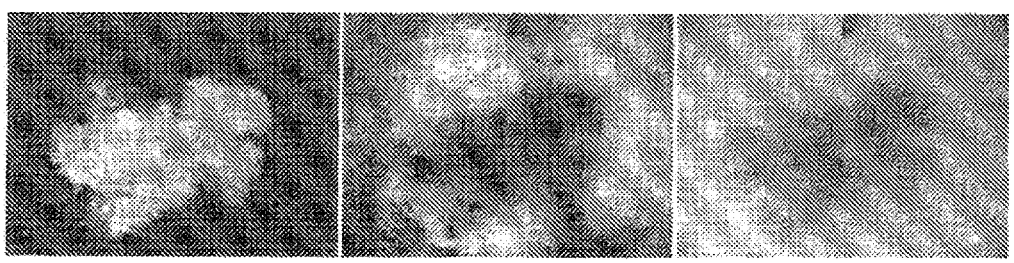
FIGS. 4a-c illustrate images from in vivo subject having LM using hyperspectral imaging and a photograph taken from the subject using conventional digital camera.

FIGS. 4a-c illustrate images from in vivo subject having LM using hyperspectral imaging and a photograph taken from the subject using conventional digital camera. In FIG. 4a an abundance map of LM is illustrated. In FIG. 4b an abundance map of healthy skin is illustrated. In FIG. 4c, a photo of the target area illustrated in FIGS. 4a and 4b is shown. In the photo of FIG. 4c the malignant tissue is shown as a dark area in the middle of the photo. The abundance map of healthy skin shows tissue that is not healthy by a dark area in the FIG. 4b. The abundance map of LM shows tissue that is LM by a light area in the FIG. 4a.

Figures 5A, 5B, 5C:
FIGS. 5a-c illustrate images from in vivo subject having LMM using hyperspectral imaging and a photograph taken from the subject using conventional digital camera.

FIGS. 5a-c illustrate images from in vivo subject having LMM using hyperspectral imaging and a photograph taken from the subject using conventional digital camera. In FIG. 5a an abundance map of LMM is illustrated. In FIG. 5b an abundance map of healthy skin is illustrated. In FIG. 5c, a photo of the target area illustrated in FIGS. 5a and 5b is shown. This tumor was on patient's ear. Depth of epidermis is very shallow, which can be seen in abundance map of skin's reflectance, where blood vessels become prominently visible. In the photo of FIG. 5c the malignant tissue is shown as a dark area in the middle of the photo. The abundance map of healthy skin shows tissue that is not healthy by a dark area in the FIG. 5b. The abundance map of LMM shows tissue that is LMM by a light area in the FIG. 5a.

Figures 6A, 6B, 6C:
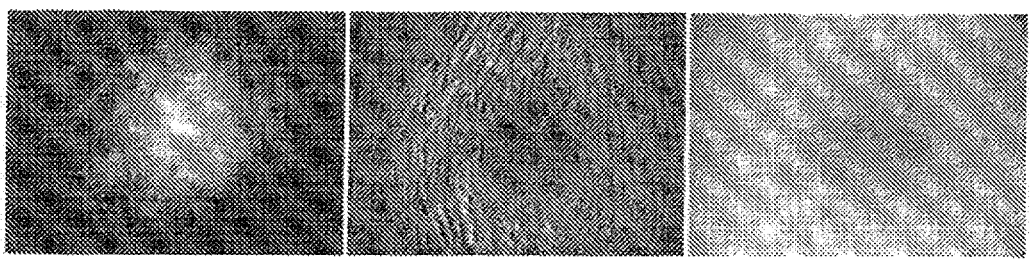
FIGS. 6a-c illustrate images from in vivo subject for Amelanotic Lentigo Maligna, Amelanotic Lentigo Maligna Melanoma and healthy skin using hyperspectral imaging and a photograph taken from the subject using conventional digital camera.

FIGS. 6a-c illustrate images from in vivo subject for amelanotic LM and amelanotic LMM using hyperspectral imaging and a photograph taken from the subject using conventional digital camera. In FIG. 6a an abundance map of amelanotic LM and amelanotic LMM are illustrated. Place of the amelanotic melanoma may be identified as increased intensity in the middle of the abundance of amelanotic LM and amelanotic LMM. In FIG. 6b an abundance of map healthy skin is illustrated. In FIG. 6c, a photo of the target area illustrated in FIGS. 6a and 6b is shown. In the photo of FIG. 6c the malignant tissue is shown as a dark area in the middle of the photo. The abundance map of healthy skin shows tissue that is not healthy by a dark area in the FIG. 6b. The abundance map of amelatonic LM and amelanotic LMM shows tissue that is malignant by a light area in the FIG. 6a.

The techniques and methods described herein may be implemented by various means. For example, these techniques may be implemented in hardware (one or more devices), firmware (one or more devices), software (one or more modules), or combinations thereof. For a hardware implementation, the arrangement of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof, for example a computer unit. The computer unit may be equipped with or connected to a display for displaying abundance maps. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the arrangement described herein may be rearranged and/or complemented by additional components in order to facilitate the achievements of the various aspects, etc., described with regard thereto, and they are not limited to the precise configurations set forth in the given figures, as will be appreciated by one skilled in the art.

Thus, according to an embodiment, the arrangement comprises processing means configured to carry out the functionalities described in any of the above embodiments. In an embodiment, at least one processor, memory and a computer program code form an embodiment of processing means for carrying out the embodiments of the invention.

Embodiments as described may also be carried out in the form of a computer process defined by a computer program. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment.

It will be obvious to a person skilled in the art that, as technology advances, the inventive concept can be implemented in various ways. Further, it is clear to a person skilled in the art that the described embodiments may, but are not required to, be combined with other embodiments in various ways.

The invention claimed is:

1. A medical imaging method, comprising:
    imaging a target with a hyperspectral imaging system in order to obtain imaging data;
    pre-processing the obtained imaging data by spatial and spectral averaging;
    selecting a number of endmembers to be determined from the pre-processed imaging data;
    extracting the endmembers from the pre-processed imaging data based on vertex component analysis on the pre-processed imaging data and the selected number of endmembers, said endmembers defining an extremity of projections of the pre-processed imaging data in a subspace spanned by the endmembers; and generating at least one abundance map of the selected number of endmembers in the pre-processed imaging data using a filter vector algorithm on the extracted endmembers and the imaging data.

2. A medical imaging method according to claim 1, wherein the pre-processed imaging data is unmixed with respect to the selected number of endmembers.

3. A medical imaging method according to claim 1, wherein the generated abundance maps are displayed.

4. A medical imaging method according to claim 1, wherein the pre-processing comprises at least one of cropping the imaging data and blurring the imaging data.

5. A medical imaging method according to claim 1, wherein the imaging data comprises a hyperspectral datacube, and wherein a pixel of the datacube comprises an intensity of light at a specific location on an imaged target for a specific wavelength of the spectrum.

6. A medical imaging method according to claim 1, wherein the endmembers correspond to at least a healthy tissue and malignant tissue.

7. A medical imaging method according to claim 1, wherein an abundance map defines borders of a specific tissue in the target.

8. A medical imaging method according to claim 1, wherein the method further comprises determining borders of dermatological lesions.

9. A medical imaging method according to claim 8, wherein the dermatological lesions comprise at least one of Lentigo Maligna (LM) or Lentigo Maligna Melanoma (LMM).

10. A medical imaging apparatus comprising:
at least one processor and at least one memory including a computer program code, wherein the at least one memory and the computer program code are configured to, with the at least one processor, cause the apparatus at least to:
obtain imaging data of a target imaged by a hyperspectral imaging system;
pre-process the obtained imaging data by spatial and spectral averaging;
select a number of endmembers to be determined from the pre-processed imaging data;
extract the endmembers from the pre-processed imaging data based on vertex component analysis on the pre-processed imaging data and the selected number of endmembers, said endmembers defining an extremity of projections of the pre-processed imaging data in a subspace spanned by the endmembers; and
generate at least one abundance map of the selected number of endmembers in the pre-processed imaging data using a filter vector algorithm on the extracted endmembers and the imaging data.

11. The medical imaging apparatus according to claim 10, wherein the at least one processor and at least one memory including the computer program code further cause the apparatus to display the generated abundance maps.

12. The medical imaging apparatus according to claim 10, further comprising a handheld hyperspectral camera for obtaining hyperspectral imaging data, said hyperspectral camera comprising a handle, a camera lens for receiving light reflected from the target, wherein a light source is arranged around the camera lens for illuminating the target, when the camera lens is towards the target, and a cone arranged around the light source and to extend towards the target.

13. The medical imaging apparatus according to claim 12, wherein a diffuse sheet is positioned between the light source and the target.

14. The medical imaging apparatus according to claim 13, wherein the diffuse sheet is fitted to the size and shape of the cone and sealed to a position inside the cone.

15. The medical imaging apparatus according to claim 12, wherein the light source is remote from the handheld camera unit and connected by a light fibre to a fiber-optic ring-light arranged around the camera lens.

16. The medical imaging apparatus according to claim 12, wherein the hyperspectral camera comprises an interface to a remote data processing unit, whereby the imaging data is sent to the data processing unit for generating at least one abundance map.

17. The medical imaging apparatus according to claim 10, wherein the preprocessing comprises at least one of cropping the imaging data and blurring the imaging data.

18. A non-transitory computer readable storage medium having stored thereon a computer program product executable by a computer processor and comprising program instructions which, when executed by the computer processor causes the computer processor to, execute the method according to claim 1.

19. The medical imaging apparatus according to claim 10, wherein the at least one processor and at least one memory including the computer program code further cause the apparatus to determine border of dermatological lesions.

* * * * *